(12) United States Patent
Stich et al.

(10) Patent No.: US 9,518,911 B2
(45) Date of Patent: Dec. 13, 2016

(54) IMPACTOR AND METHOD FOR CHARACTERIZING A CARRIER GAS ENRICHED WITH SUSPENDED PARTICLES

(75) Inventors: Ralf Stich, Buchenbach (DE); Michael Laufer, Freiburg (DE); Jürgen Bär, Friedenweiler (DE)

(73) Assignee: Testo AG, Lenzkirch (DE)

( * ) Notice: Subject to any disclaimer, the term of this patent is extended or adjusted under 35 U.S.C. 154(b) by 543 days.

(21) Appl. No.: 14/003,326

(22) PCT Filed: Mar. 6, 2012

(86) PCT No.: PCT/EP2012/000997
§ 371 (c)(1),
(2), (4) Date: Nov. 15, 2013

(87) PCT Pub. No.: WO2012/123078
PCT Pub. Date: Sep. 20, 2012

(65) Prior Publication Data
US 2014/0053630 A1   Feb. 27, 2014

(30) Foreign Application Priority Data

Mar. 11, 2011   (DE) .................. 10 2011 013 697

(51) Int. Cl.
| | | |
|---|---|---|
| G01N 15/06 | (2006.01) | |
| G01N 5/02  | (2006.01) | |
| G01N 15/02 | (2006.01) | |

(52) U.S. Cl.
CPC ............ *G01N 15/0618* (2013.01); *G01N 5/02* (2013.01); *G01N 15/0255* (2013.01); *G01N 15/0606* (2013.01); *G01N 2015/0261* (2013.01)

(58) Field of Classification Search
CPC ............ G01N 15/0255; G01N 15/0606; G01N 15/0618; G01N 5/02; G01N 2015/0261
See application file for complete search history.

(56) References Cited

U.S. PATENT DOCUMENTS

| | | | | |
|---|---|---|---|---|
| 4,321,822 A | * | 3/1982 | Marple | ............... G01N 1/2208 73/28.06 |
| 6,431,014 B1 | | 8/2002 | Liu et al. | |

(Continued)

FOREIGN PATENT DOCUMENTS

| | | |
|---|---|---|
| DE | 10061976 | 6/2001 |
| DE | 102005056718 | 5/2007 |

(Continued)

OTHER PUBLICATIONS

Klaus, N. et al., "Ein Kaskadenimpaktor Mit Rotierenden Stauplatten", pp. 168-170, Reinhaltung Der Luft (1985).

(Continued)

*Primary Examiner* — Hezron E Williams
*Assistant Examiner* — David Z Huang
(74) *Attorney, Agent, or Firm* — Volpe and Koenig, P.C.

(57) ABSTRACT

In the case of an impactor (1) with an impact plate (7) and a classifying nozzle (2) directed at this impact plate (7), in the case of which the impact plate (7) is formed as an electronically readable resonantly oscillating, mass-sensitive element (7, 33), it is proposed to move the oscillating crystal (7, 33) held in an impact plate holder (8) in relation to the static classifying nozzle (2) by a motor (12) during the operation of the impactor (1).

18 Claims, 7 Drawing Sheets

(56) References Cited

U.S. PATENT DOCUMENTS

| | | | |
|---|---|---|---|
| 2002/0124632 A1 | 9/2002 | Reiter et al. | |
| 2004/0209505 A1* | 10/2004 | Wade .................... | B60R 16/027 439/164 |
| 2005/0028616 A1 | 2/2005 | Marple et al. | |
| 2005/0172735 A1 | 8/2005 | Booker | |
| 2005/0247868 A1 | 11/2005 | Call et al. | |
| 2010/0083737 A1 | 4/2010 | Paur et al. | |

FOREIGN PATENT DOCUMENTS

| | | |
|---|---|---|
| DE | 102007013938 | 9/2008 |
| EP | 1957955 | 8/2008 |
| WO | 2007062818 | 6/2007 |

OTHER PUBLICATIONS

Figure 1:
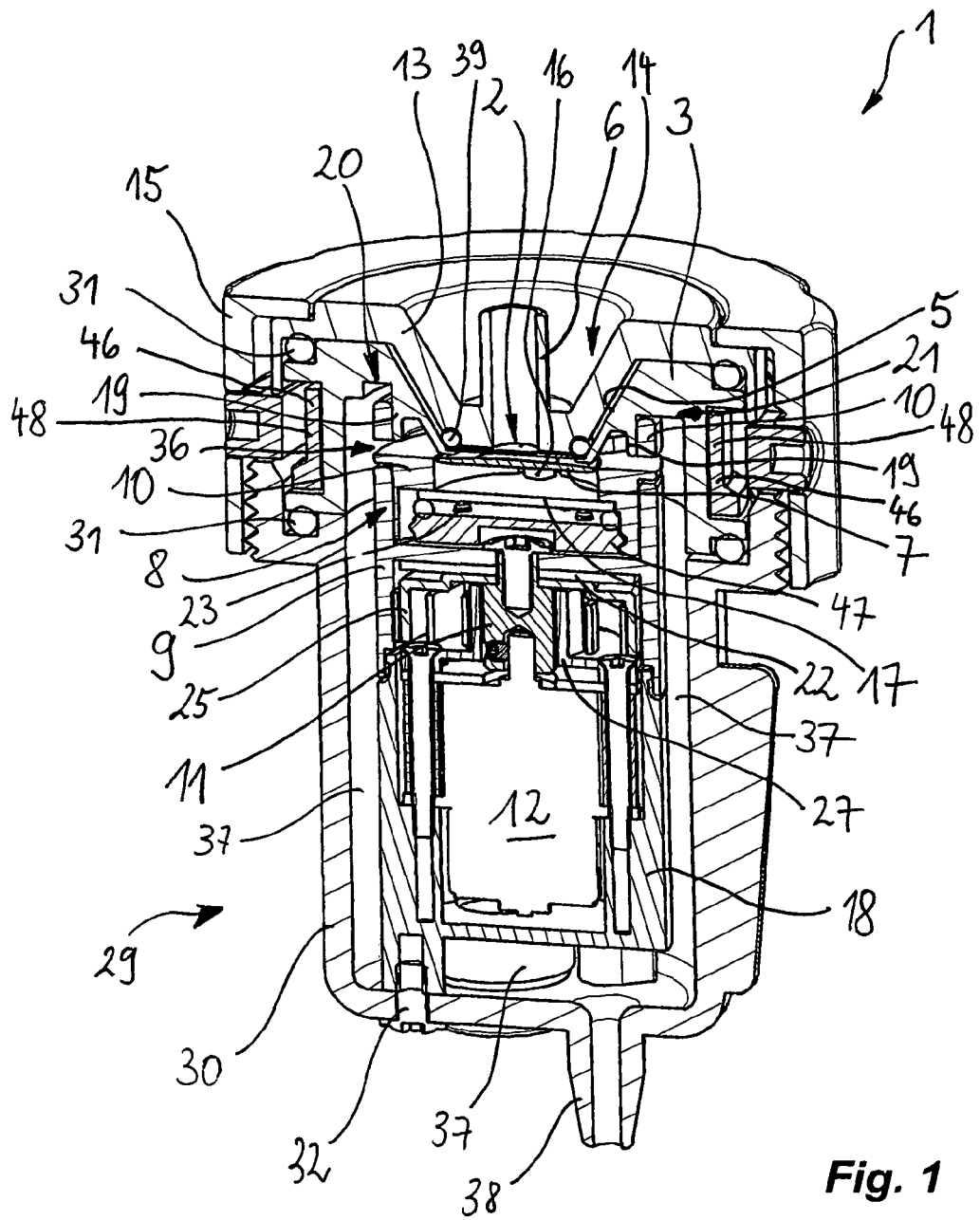
Figure 2:
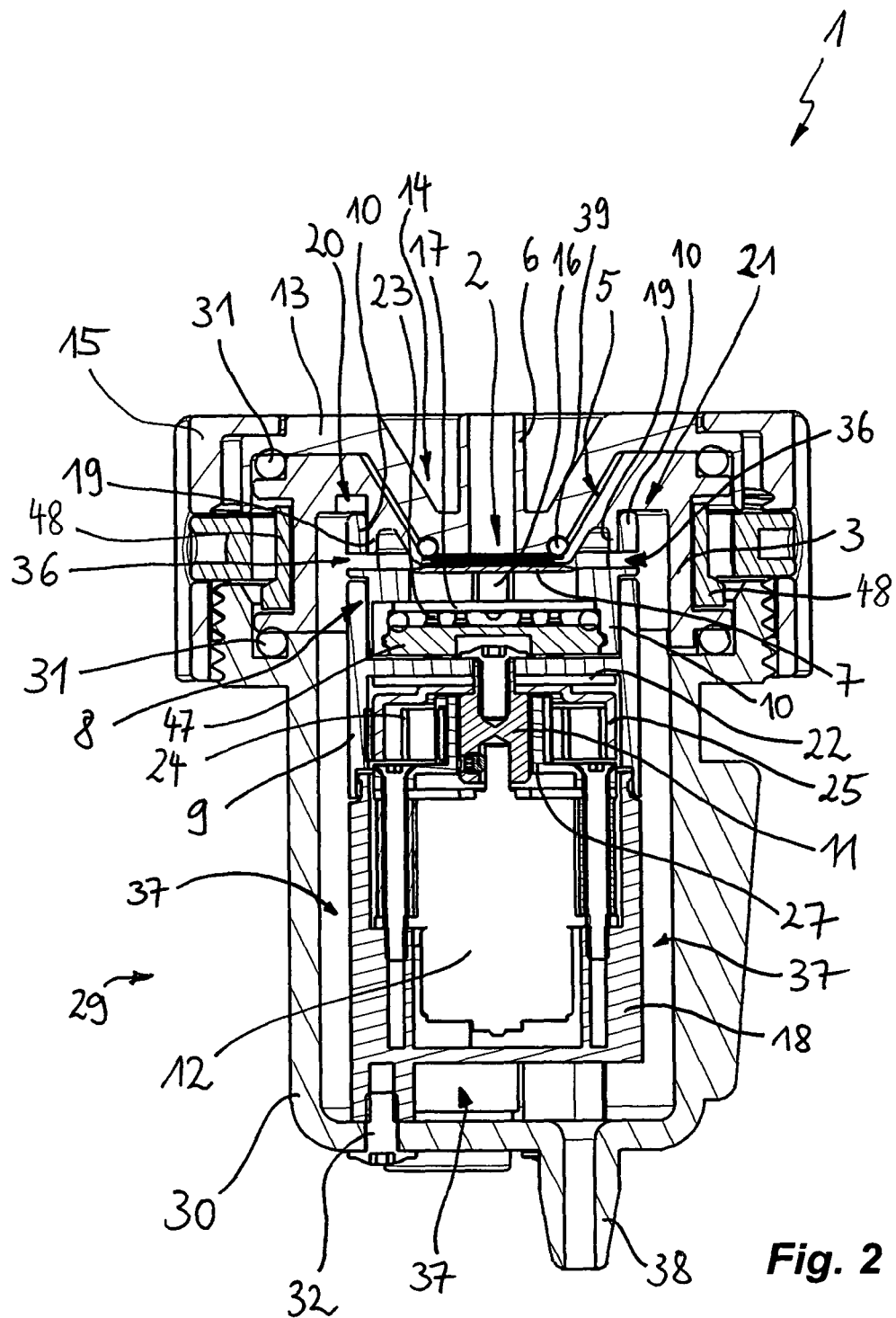

Ho, Matt H., "Applications of Quartz Crystal Micro-Balances in Aerosol Mass Measurement", Dec. 31, 1984, Elsevier, Amsterdam, vol. 7, pp. 351-388, p. 358-p. 359, Figure 1a.

\* cited by examiner

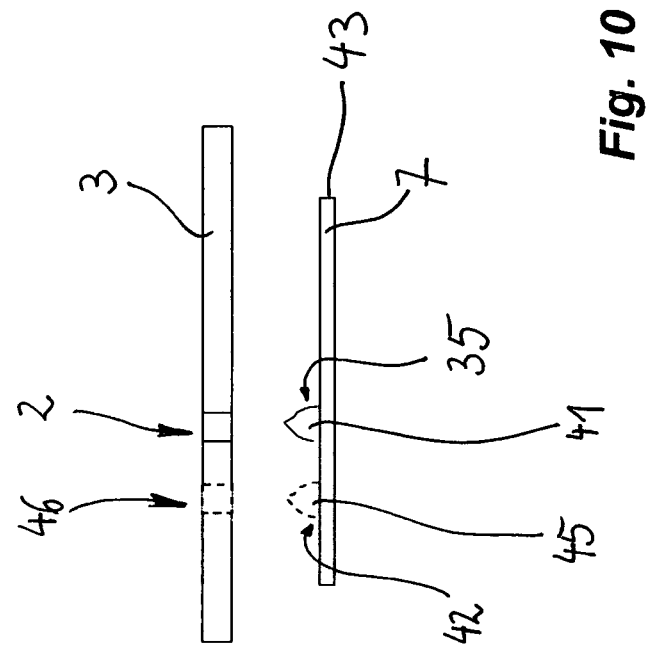
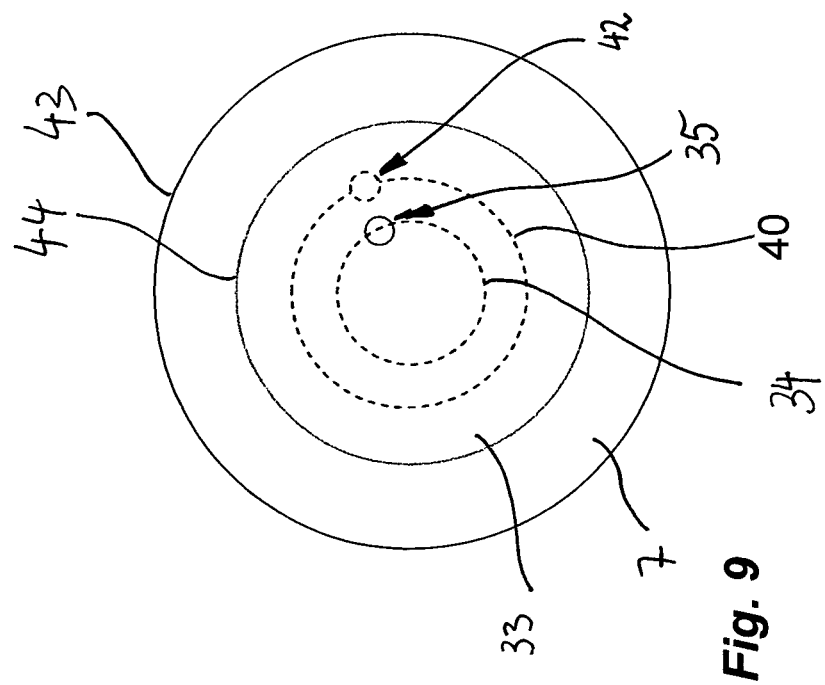
Fig. 10
Fig. 9

IMPACTOR AND METHOD FOR CHARACTERIZING A CARRIER GAS ENRICHED WITH SUSPENDED PARTICLES

BACKGROUND

The invention concerns an impactor for the analysis of a carrier gas enriched with suspended particles, with a classifying nozzle unit having at least one classifying nozzle and with an impact plate, the impact plate being formed as an oscillating crystal and the resonantly oscillating, mass-sensitive element being secured in an impact plate holder.

The invention also concerns a method for characterizing a carrier gas enriched with suspended particles, the carrier gas enriched with suspended particles being conducted in an impactor through a classifying nozzle onto a resonantly oscillating, mass-sensitive element acting as an impact plate in such a way that, as from a prescribed mass, suspended particles are deposited in a depositing process on the resonantly oscillating, mass-sensitive element, and the mass of the suspended particles deposited on the resonantly oscillating, mass-sensitive element being determined electronically during the depositing process and/or between two depositing processes.

Such an apparatus and such a method are known, for example, from EP 1 957 955 B1, in which the oscillating crystal is held at three points arranged rotationally symmetrically in relation to one another about its normal axis of symmetry. The use of an oscillating crystal offers the advantage over films for receiving the deposited suspended particles that measurement of the deposited mass is possible without removal of the impact plate.

The invention is based on the object of improving the functional properties of an impactor.

SUMMARY

To achieve this object, it is provided in the case of an impactor of the type mentioned at the beginning that the impact plate holder is arranged such that it can be moved in relation to the classifying nozzle by a motor. The impactor may consequently have a motor by which a movement of the impact plate holder with the resonantly oscillating, mass-sensitive element can be driven. It is of advantage in this case that the depositing location of the suspended particles on the resonantly oscillating, mass-sensitive element can be changed during the depositing process and/or between two successive depositing processes, so that the surface area offered by the resonantly oscillating, mass-sensitive element can be utilized better. Therefore, exchanging or cleaning the fully loaded oscillating crystal is only required at relatively great intervals, which significantly improves the functional properties of the impactor. Therefore, for uniform loading of the impact plate, with the invention it is no longer necessary to provide multiple classifying nozzles in parallel arrangement by which the carrier gas is directed onto the impact plate.

For the purposes of the invention, a resonantly oscillating, mass-sensitive element is understood as meaning an electrically or electronically readable element that has a mass-dependent resonant frequency. The resonant frequency is electrically or electronically readable. For example, the resonantly oscillating, mass-sensitive element may be formed as an oscillating crystal or as an SAW element, that is to say an element responding to acoustic surface waves, or as an element based on another measuring principle. If an oscillating crystal is held on the impact plate holder, the impact plate holder may also be referred to as an oscillating crystal holder.

Particularly simple sequences of movements can be achieved if the impact plate holder is arranged rotatably or pivotably about an axis. It can consequently be achieved, for example, that the point of impingement on the impact plate of the carrier gas enriched with suspended particles migrates on the impact plate along an arc of a circle or along a circle, the center point coinciding with the axis of the rotating or pivoting movement.

For cleaning and/or exchanging the classifying nozzle, it may be provided that the classifying nozzle is removably arranged in the impactor.

To achieve favorable through-flowing properties, it may be provided that the classifying nozzle is formed so as to be heatable. Preferably, an annular heater which surrounds the classifying nozzle and/or the classifying nozzle unit annularly on the outside may be provided.

In order to maintain a defined distance between the impact plate and the classifying nozzle in a simple way, it may be provided that the impact plate holder bears against or is supported on the classifying nozzle unit. This is particularly favorable in combination with a removable classifying nozzle and/or with a removable impact plate holder.

In order to be able to maintain a prescribed sequence of movements as exactly as possible, it may be provided that the impact plate holder is radially guided with respect to the axis of a rotating or pivoting movement on the classifying nozzle unit. It is of advantage in this case that defined geometrical conditions can be maintained in a simple way even during the movement of the impact plate holder in relation to the classifying nozzle.

It has been found that different mass sensitivities can be achieved with resonantly oscillating, mass-sensitive elements, that is to say that different resonantly oscillating, mass-sensitive elements respectively show an individual dependence of the change in resonant frequency when there is a prescribed increase in mass. This mass sensitivity depends on the position of the point of impingement of the carrier gas on the surface of the resonantly oscillating, mass-sensitive element, in particular on the distance of the point of impingement from the periphery or clamping point of the element. It is therefore particularly favorable if the point of impingement is guided by the relative movement according to the invention along a line of constant mass sensitivity.

In the case of an element that is round in the form of a disk, these lines are, for example, circles or arcs of circles.

In this case and many other cases, a rotating or pivoting movement of which the rotating or pivoting axis coincides with the center point of the circles and/or a centroid of the resonantly oscillating, mass-sensitive element is particularly advantageous.

In the case of a refinement of the invention, it may be provided that the impact plate holder is at least radially guided on a motor housing of the motor. It is of advantage in this case that a defined rotating or pivoting movement of the impact plate holder can be achieved by simple means. It is particularly favorable if the impact plate holder is radially guided on its side facing the motor housing by the motor housing and on its side facing the classifying nozzle unit by the classifying nozzle unit, so that guidance of the impact plate holder on both sides during the rotating or pivoting movement is obtained.

It is particularly favorable if the classifying nozzle unit has on its side facing the resonantly oscillating, mass-sensitive element a guiding means for the radial and/or axial guidance of the impact plate holder. Such a guiding means may, for example, be formed as a guiding groove and/or as a guiding collar or as a guiding projection.

In the case of a refinement of the invention, it may be provided that a stop which limits the rotating or pivoting movement of the impact plate holder about the axis with respect to a full circle is formed on a rotatable or pivotable part and/or on a stationary part, for example on the classifying nozzle unit and/or on the impact plate holder. For example, the stop may be formed as a projection which engages in a guiding groove which is formed along the limited rotating or pivoting range. It is of advantage in this case that over-rotation of the impact plate holder with respect to the stationary parts of the impactor is achieved in a simple way. This allows electrical signals to be passed from and/or to the resonantly oscillating, mass-sensitive element by way of a connecting cable, and the use of sliding contacts to be avoided.

In the case of a refinement of the invention, it may be provided that the impact plate holder has a holding plate on which the oscillating crystal is held. It is of advantage in this case that on the one hand the oscillating crystal can be fixed in a defined position in a simple way and that on the other hand the oscillating crystal can be exchanged in a simple way.

It may be provided that the impact plate holder has resilient contact pins which in the position for use contact the holding plate, preferably on the underside of the holding plate. It is of advantage in this case that the electrical connection of an exchangeable oscillating crystal can be established in a simple way.

For the transmission of the electrical signals from or to the resonantly oscillating, mass-sensitive element, it may be provided that the contact pins and/or the resonantly oscillating, mass-sensitive element is/are electrically connected to a flexible connecting cable.

It is particularly favorable in this case if the connecting cable is dimensioned such that a rotating or pivoting movement of the impact plate holder is made possible within a prescribed rotating or pivoting range.

For example, the length of the connecting cable may be dimensioned such that the rotating or pivoting movement is not prevented by the connecting cable within the prescribed range of movement.

For example, it may be provided that the connecting cable is configured as a flat ribbon cable.

It is of advantage in this case that a flat ribbon cable has a preferential direction for bends which can be aligned such that a rotating or pivoting movement of the impact plate holder is impaired as little as possible by the connecting cable.

For the further processing of the electrical signals of the resonantly oscillating, mass-sensitive element and/or for the activation of the resonantly oscillating, mass-sensitive element and/or for further functions, it may be provided that the connecting cable is electrically connected to an evaluation electronics unit for the resonantly oscillating, mass-sensitive element.

For the execution of the relative movement between the impact plate holder and the classifying nozzle, it is possible, for example, for the motor to be coupled with the impact plate holder by way of a transmission mechanism, or it may be provided that the motor is electrically activated for the execution of a possibly limited movement.

It is particularly favorable if the motor is a stepping motor. It is of advantage in this case that the position of the motor, and consequently the movement of the impact plate holder, can be controlled with particular precision. The motor may also be a DC motor.

For the provision of a robust impactor that is suitable for many areas of use, it may be provided that the motor is arranged with the impact plate holder in an outwardly sealed encapsulation. For example, the encapsulation may be formed by a housing pot, in which for example the motor is arranged, and a housing cover, the two parts being able to be releasably connected to one another. After the release of the connection, it is thus easily possible to get to the parts of the impactor lying inside.

For the setting up of the rotating or pivoting movement, it may be provided that an activation electronics unit or an activation mechanism with which a change of direction and/or a limitation of the rotating or pivoting angle of the rotating or pivoting movement can be brought about is formed for the rotating or pivoting movement of the impact plate holder. For example, this may be set up by a crank mechanism, or a stepping motor may be electronically activated according to a prescribed program of sequences.

It may be provided that the impact plate holder has a heating device. It is of advantage in this case that in this way a temperature drift of the mass-dependent resonant frequency of the resonantly oscillating, mass-sensitive element can be prevented. Preferably, the heating device is connected to the or a flexible connecting cable.

To achieve a uniform distribution of the deposited suspended particles on the resonantly oscillating, mass-sensitive element, it may be provided that the classifying nozzle has a through-opening which is arranged eccentrically with respect to the axis.

For example, the classifying nozzle may have a single through-opening. It is of advantage in this case that a classifying nozzle that is particularly simple to produce is provided.

According to an invention of independent significance, it may be provided in the case of an impactor of the type described at the beginning that the classifying nozzle is set up such that it can be changed, in particular can be displaced and/or can be exchanged, in order to displace a point of impingement of the carrier gas conducted through the classifying nozzle on the resonantly oscillating, mass-sensitive element transversely in relation to a line of constant mass sensitivity. It is of advantage in this case that the mass sensitivity of the resonantly oscillating, mass-sensitive element is adaptable to a desired sensor sensitivity and/or to an existing range of values of an evaluation electronics unit.

The changing may take place by exchanging the classifying nozzle for another classifying nozzle, the at least one through-opening of which is in a different position than in the case of the first classifying nozzle. In this case, the impactor comprises at least two classifying nozzles which are arranged or kept such that they can be exchanged for one another.

The changeability may be additionally or alternatively set up by a movable arrangement of the classifying nozzle in a classifying nozzle unit.

It may also be provided that the impact plate holder is arranged movably and/or traversably along a second axis.

If, for example, the line is given by a circle or an arc of a circle—as described above—the changing of the point of impingement may take place in a radial direction with respect to the circle and/or a center of the rotating or pivoting movement.

To achieve the object in the case of a method of the type mentioned at the beginning, it is provided according to the invention that the resonantly oscillating, mass-sensitive element is moved in relation to the static classifying nozzle during the depositing process and/or between two depositing processes. This allows a uniform utilization of the surface of the resonantly oscillating, mass-sensitive element to be achieved, whereby the number of necessary maintenance measures per unit of time can be reduced. As a result, the method is simplified.

The movement may be executed continuously and/or at specific time intervals and/or after a specific loading with suspended particles at a point of impingement.

For example, the movement may be executed as a rotating or pivoting movement. It is of advantage in this case that the depositing location on the resonantly oscillating, mass-sensitive element can be guided along an arc of a circle or a full circle. To compensate for a temperature dependence of the mass-dependent resonant frequency of the resonantly oscillating, mass-sensitive element, it may be provided that the resonantly oscillating, mass-sensitive element is heated during the depositing process. Preferably, the heating takes place electrically.

A refinement that can be realized in a simple manner with favorable utilization of the surface of the resonantly oscillating, mass-sensitive element may provide that the resonantly oscillating, mass-sensitive element is rotated or pivoted about an axis in relation to the classifying nozzle.

Here it may be provided that the rotating or pivoting movement is limited with respect to a full circle.

It is of advantage in this case that excessive winding up or rupturing of a connecting cable between the movable oscillating crystal and a stationary electronics unit is avoidable.

To achieve a periodically recurring movement, it may be provided that the direction of the rotating or pivoting movement is reversed during the movement.

An invention of independent significance may provide in the case of the method described at the beginning that, during the depositing process and/or between two depositing processes, a point of impingement of the carrier gas conducted through the classifying nozzle on the resonantly oscillating, mass-sensitive element is displaced on the resonantly oscillating, mass-sensitive element transversely in relation to a line of constant mass sensitivity.

If the relative movement of the resonantly oscillating, mass-sensitive element is executed by a rotating or pivoting movement, it may be provided that the point of impingement is displaced in a radial direction.

It may also be provided that the classifying nozzle is exchanged for another classifying nozzle, the at least one through-opening of which is formed at a position which corresponds to a line of changed mass sensitivity.

BRIEF DESCRIPTION OF THE DRAWINGS

The invention is now described in more detail on the basis of an exemplary embodiment, but is not restricted to this exemplary embodiment. Further exemplary embodiments are obtained by combining individual or multiple features of the claims with one another and/or with individual or multiple features of the exemplary embodiment.

In the drawings:

FIG. 1 shows an impactor according to the invention in a three-dimensional sectional view, FIG. 2 shows the sectional view as shown in FIG. 1 in an axial sectional representation, FIG. 3 shows the parts arranged in the interior of the encapsulation of the impactor according to the invention as shown in FIG. 1 in a three-dimensional sectional view, FIG. 4 shows the sectional view as shown in FIG. 3 in an axial sectional representation, FIG. 5 shows a radial section through the parts arranged in the interior of the encapsulation of the impactor according to the invention as shown in FIG. 1 at the level of the spirally wound-up connecting cable in a view from below in the direction of the impact plate, FIG. 6 shows the sectional representation as shown in FIG. 5 in the opposite viewing direction of the motor, FIG. 7 shows a three-dimensional perspective view of the classifying nozzle unit of the impactor according to the invention as shown in FIG. 1, FIG. 8 shows a basic representation for explanation of the method according to the invention, FIG. 9 shows a basic representation for further explanation of the invention in the viewing direction of the resonantly oscillating, mass-sensitive element acting as an impact plate, and FIG. 10 shows a further basic representation for explanation of the invention as shown in FIG. 9 in an axial sectional view from the side.

DETAILED DESCRIPTION OF THE PREFERRED EMBODIMENTS

In the following, the figures are described together.

FIG. 1 and FIG. 2 show sectional representations of an impactor according to the invention that is designated as a whole by 1.

The impactor 1 has a classifying nozzle 2, which is formed on a classifying nozzle unit 3.

The classifying nozzle 2 is formed here as an opening in the removable and consequently exchangeable base 4 of a pot-shaped recess with a frustoconical side wall 5 of the classifying nozzle unit 3.

The carrier gas to be investigated, which contains suspended particles, is fed to the classifying nozzle 2 by way of a tube or the like connected to the connecting stub 6 and is conducted through this nozzle onto an impact plate 7.

The impact plate 7 is arranged so closely behind the classifying nozzle 2 that only suspended particles of which the mass lies below a specific value can follow the stream of carrier gas deflected by the impact plate. The other suspended particles impinge on the impact plate 7 and are deposited there.

The impact plate 7 is formed in a way known per se as a resonantly oscillating, mass-sensitive element, in the example as an oscillating crystal of which the resonant or natural frequency is mass-dependent. This has the consequence that the resonant frequency of the resonantly oscillating, mass-sensitive element changes when suspended particles are deposited on the surface.

The resonant frequency of the resonantly oscillating, mass-sensitive element is detected in a way known per se by an electronic sweep signal, without the impact plate 7 having to be removed from the impactor 1 for this purpose.

Consequently, online measurements of the deposited mass are possible.

As can be seen more specifically in FIG. 4 and FIG. 5, the impact plate 7 is arranged in an impact plate holder 8.

The impact plate holder 8 has here a holding ring 10 and a terminating plate 47, which is fitted in a conjointly rotating manner in a holding bush 9 not belonging to the impact plate holder.

In the exemplary embodiment represented, the impact plate holder 8 comprises the resonantly oscillating, mass-sensitive element 7, the securing elements 16, the holding ring 10, the holding plate 17 and the terminating plate 47.

The impact plate holder 8 is formed such that it can be removed from the holding bush 9.

The impact plate holder 8 is connected to the output shaft of a motor 12 by way of a driver 11.

The impact plate holder 8 is therefore arranged movably in the impactor 1 and can be pivoted or rotated by the motor 12 about the axis of the motor.

The classifying nozzle 2 is arranged in the impactor 1 such that it can be removed with the classifying nozzle unit 3. For this purpose, the housing cover 13, the frustoconical depression 14 of which is formed so as to fit the pot-shaped recess comprising the base 4 and the side wall 5 of the classifying nozzle unit 3 and is fitted in this recess in the position for use, may be removed by releasing and removing the connecting element 15, in the exemplary embodiment a union nut.

For controlling the temperature of the classifying nozzle 2, there is a heater 48, which surrounds the classifying nozzle unit 3 annularly on the outside.

With the classifying nozzle unit 3 removed, the holding ring 10 is exposed and can then likewise be removed in order to get to the impact plate 7.

The impact plate 7 is secured and electrically connected to a holding plate 17 by way of two securing elements 16 acting on opposite sides of the impact plate 7. The holding plate 17 is formed as a circuit board and provides the electrical contacting for the resonantly oscillating, mass-sensitive element 7. Apart from the securing elements 16, the holding plate 17 has a heater that cannot be seen any further. It may also have a memory module. The heater prevents the signal of the crystal from being exposed to thermal influences. The memory module may serve the purpose that in each crystal module or for each resonantly oscillating, mass-sensitive element 7, specific data can be stored.

In the mounted position, the classifying nozzle unit 3 acts on the holding ring 10 of the impact plate holder 8. Consequently, the impact plate holder 8 is supported on the classifying nozzle unit 3, and the holding plate 17 with the impact plate 7 is fixed by the holding ring 10.

The holding bush 9 extends over the motor housing 18 of the motor 12 axially in a partial region, whereby the rotating or pivoting movement of the impact plate holder 8 is radially guided.

Formed on the inner side of the classifying nozzle unit 3 is a guiding means 19—in the exemplary embodiment a peripheral, inwardly projecting collar—, which radially guides the impact plate holder 8 by way of the holding ring 10 bearing radially on the outside.

Incorporated on the inner side of the classifying nozzle unit 3 is a peripheral groove 20, which runs almost around a full circle but is interrupted at one point of the circumference. In this way, a stop 21 is formed for a projection on the holding ring 10 that engages in the groove 20 but cannot be seen any further.

This stop 21 thereby prevents the impact plate holder 8 from being able to rotate by a full circle. Rather, the rotating or pivoting movement of the impact plate holder 8 about its axis is limited with respect to a full circle, and the motor 12, in the exemplary embodiment a stepping motor, is activated by an activation electronics unit not represented any further but known per se such that, with the oscillating crystal 7 acting as an impact plate, the impact plate holder 8 is moved between the end points of the rotating or pivoting movement by the direction of the rotating or pivoting movement being reversed in a periodically recurring manner.

Fitted between the holding ring 10 and the holding bush 9 is a circuit board 22, on the upper side of which, that is to say the side of which that is facing the impact plate 7 and the holding plate 17, resilient contact pins 23 are arranged.

The contact pins 23 are arranged regularly, and consequently act uniformly on the holding plate 17.

The contact pins 23 contact electrical connecting traces that cannot be seen any further but are known per se on the underside of the holding plate 17, and thus establish an electrical contact between the holding plate 17 and a connecting cable 24.

Figure 5:
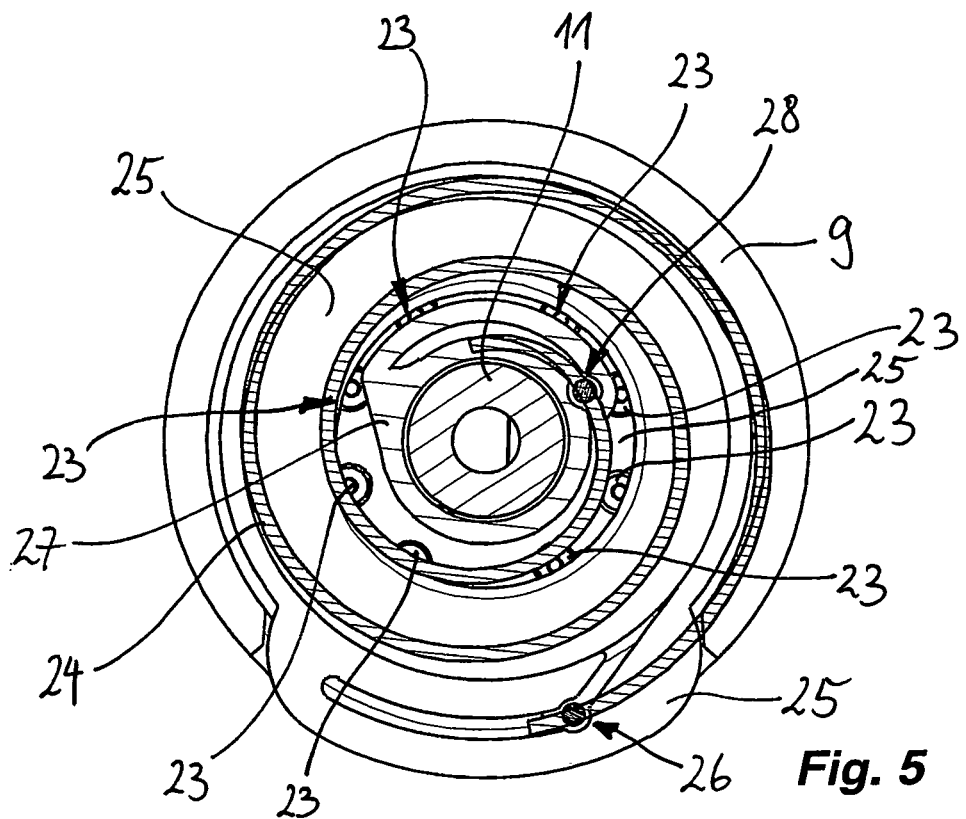
Figure 6:
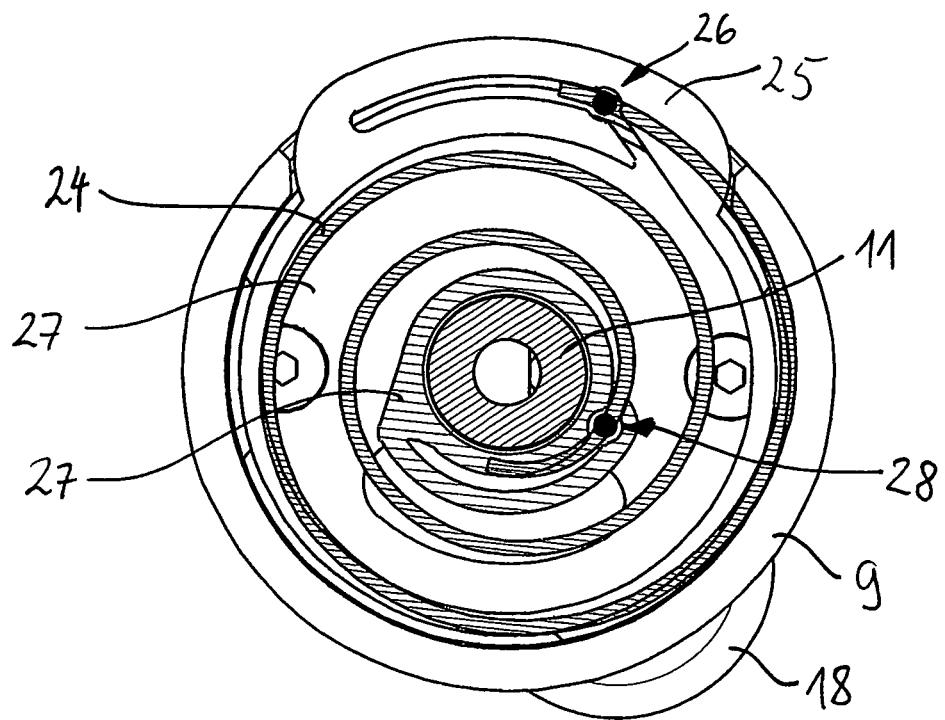
Figure 7:
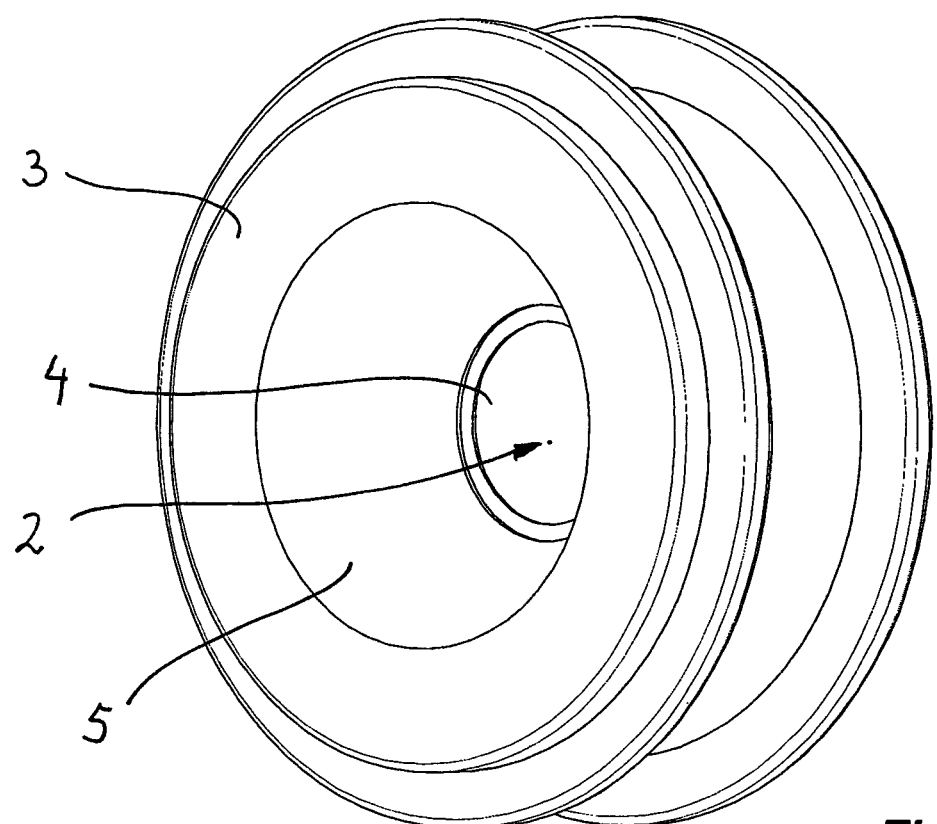

As can be seen in sectional representations in FIG. 5 and FIG. 6, the connecting cable 24 is spirally wound up.

The connecting cable 24, produced as a flat ribbon, consequently forms a flexible connecting cable 24, which does not prevent the rotating or pivoting movement of the impact plate holder 8 within the desired range of movement.

The connecting cable 24 is fixed at its radially outer end to an upper cable covering 25, which is connected in a conjointly rotating manner to the impact plate holder 8 and is electrically connected by way of a fixing means 26 to the contact pins 23 led through the upper cable covering 25.

The connecting cable 24 is formed as an eight-conductor flat ribbon cable, which is connected to the eight contact pins 23. Other numbers of conductors and of contact pins 23 can also be realized.

At its radially inner end, the connecting cable 24 is fixed to a lower cable covering 27, which is connected in a conjointly rotatable manner to the motor housing 18 and remains stationary.

The eight-conductor connecting cable 24 is connected by way of a fixing means 28 to an activation electronics unit that is not represented any further.

The lower cable covering 27 and the upper cable covering 25 enclose or surround the connecting cable 24 in such a way as to form a housing. The motor 12 with the motor housing 18 and the impact plate holder 8 with the associated superstructures are arranged in an encapsulation 29, which is formed by the housing cover 13, a housing pot 30 and the classifying nozzle unit 3 fitted between them.

The encapsulation 29 is outwardly sealed by seals 31.

The motor housing 18 is secured to the housing pot 30 by means of securing elements 32—in the exemplary embodiment screws.

The housing pot 30 is dimensioned such that the motor 12 with the parts connected thereto is completely accommodated.

By way of the connecting cable 24, electrical heating energy is fed to a heating device that is arranged in the impact plate holder 8 but cannot be seen any further, in order to keep the resonantly oscillating, mass-sensitive element 7 at a desired temperature.

Figure 8:
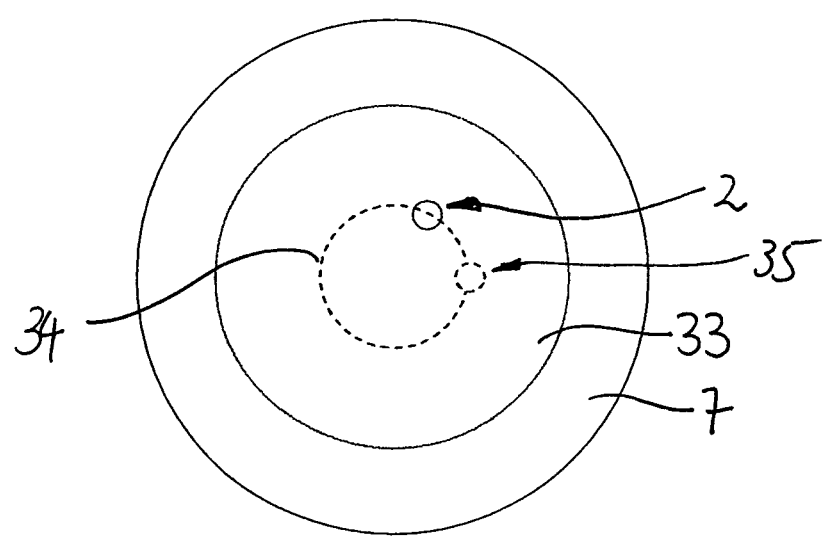

FIG. 8 shows a plan view of the impact plate 7 with the oscillating crystal region 33 formed as round, in the form of a disk.

A possible position of the classifying nozzle 2 in the direction of flow of the carrier gas ahead of the impact plate 7 is represented.

It can be seen that the classifying nozzle 2 is arranged eccentrically with respect to the center of the disk of the resonantly oscillating, mass-sensitive element, which at the same time represents the axis of the rotating or pivoting movement.

By means of the motor 12, the impact plate 7 is rotated about its axis, so that the classifying nozzle 2 arrives in a new position 35 over the impact plate 7 along an arc of the circle 34.

This achieves the effect that the depositing of the heavy suspended particles on the impact plate 7 can be continued in another region of the resonantly oscillating, mass-sensitive element 33 that has not so far been exposed to the classifying nozzle 2, or only slightly.

The carrier gas with the light suspended particles that are not deposited on the impact plate 7 flows by way of through-openings 36 and a channel 37 surrounding the motor housing 18 to an outlet stub 38 on the housing pot 30, from where it is sucked in by a pump not represented any further but known per se, by way of a tube or the like.

FIG. 9 shows a view from above of the resonantly oscillating, mass-sensitive element 7 with the oscillating crystal region 33 formed in the example as circularly round.

On the resonantly oscillating, mass-sensitive element 7 there are lines 34, 40 of constant mass sensitivity. As a result of the circularly round form of the resonantly oscillating, mass-sensitive element 7, the lines 34, 40 describe concentric circles. In the case of other geometrical forms of the element 7, different lines are formed.

The lines 34, 40 are often described by a constant distance from the periphery 43 of the element 7 and/or from the periphery 44 of the oscillating crystal region 33 (or of the corresponding mass-sensitive region in the case of a different element).

If—as shown in FIG. 8—the point of impingement 35 migrates along the line 34, a deposition of a prescribed mass of suspended particles 41 brings about a respectively similar change in the resonant frequency of the resonantly oscillating, mass-sensitive element 7.

The classifying nozzle 3 is thus set up such that it can be changed in such a way that a point of impingement 35 of the carrier gas conducted through the classifying nozzle is displaced on the resonantly oscillating, mass-sensitive element 7, 33 transversely in relation to a line 34 of constant mass sensitivity.

In the simplest case, this is achieved by exchanging the classifying nozzle 3 for another classifying nozzle 3, which has a through-opening 46 at a position offset transversely in relation to the line 34 with respect to the through-opening 2.

Alternatively, in the case of a further exemplary embodiment, the classifying nozzle 3 and the element 7 may be arranged displaceably with respect to one another and be displaced such that the point of impingement 35 moves transversely in relation to the line 34 away from the line 34 on the surface of the element.

By way of example, a new point of impingement 42 is depicted radially outside the point of impingement 35. It is also possible to include points of impingement inside the circle 34.

Figure 3:
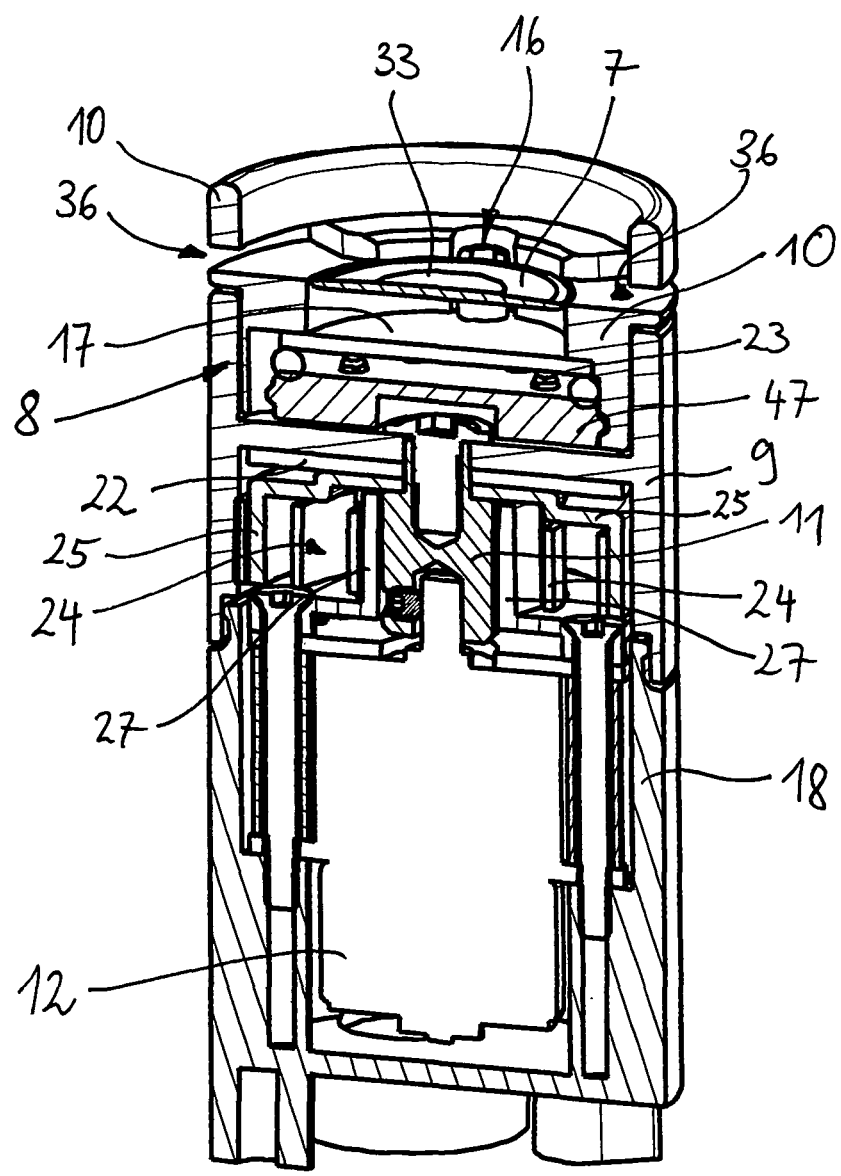
Figure 4:
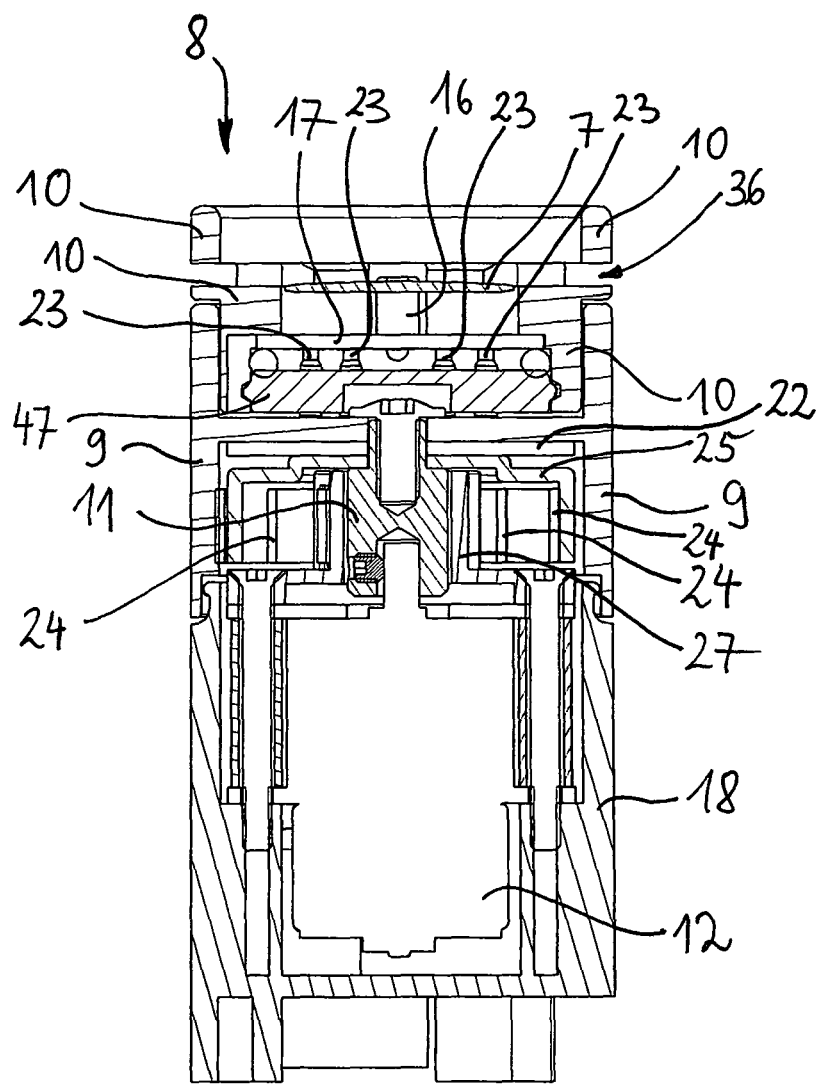

In the case of the new point of impingement 42, a changed dependence of the resonant frequency of the element 7 on the deposited mass of suspended particles 41, 45 is obtained. It is often the case that a line 40 arranged closer to the clamping point (in FIG. 3, this takes the form of the securing elements 16 acting on the periphery 43) of the resonantly oscillating, mass-sensitive element 7 in the impact plate holder 8 has an increased variability of the resonant frequency of the deposited mass of suspended particles 41, 45 in comparison with a line 34 arranged further away.

If the rotating or pivoting movement of the resonantly oscillating, mass-dependent element 7 is executed further toward the classifying nozzle 3, the point of impingement 42 migrates along the arc or circle 44, as described in relation to FIG. 8.

In the case of the impactor 1 with an impact plate 7 and a classifying nozzle 2 directed at this impact plate 7, in the case of which the impact plate 7 is formed as an electronically readable oscillating crystal 7, 33, it is proposed to move the oscillating crystal 7, 33 held in an impact plate holder 8 in relation to the static classifying nozzle 2 by a motor 12 during the operation of the impactor 1.

The invention claimed is:

1. An impactor (1) for analysis of a carrier gas enriched with suspended particles, comprising a classifying nozzle unit (3) having at least one classifying nozzle (2) and with just one impact plate (7), the impact plate (7) being formed as a resonantly oscillating, mass-sensitive element (7, 33) and the resonantly oscillating, mass-sensitive element (7, 33) being secured in an impact plate holder (8), the impact plate holder (8) is arranged to be movable in relation to the classifying nozzle (2) by a motor (12), so that a point of impingement (35) of the carrier gas enriched with suspended particles on the impact plate (7) migrates along an arc of a circle or along a circle, a center point coinciding with an axis of a rotating or pivoting movement, on the impact plate (7) and a depositing location of the suspended particles on the resonantly oscillating, mass-sensitive element is changeable during a depositing process, the point of impingement being guided by relative movement along a line of constant mass sensitivity, the resonantly oscillating, mass-sensitive element (7, 33) is electrically connected to a flexible connecting cable (24) that is dimensioned such that the rotating or pivoting movement of the impact plate holder (8) is made possible within a prescribed rotating or pivoting range, and the impact plate holder (8) has a holding plate (17) on which the resonantly oscillating, mass-sensitive element (7, 33) is held, and the impact plate holder (8) has resilient contact pins (23) that are arranged regularly, which in a position for use, act uniformly on the holding plate (17).

2. The impactor (1) as claimed in claim 1, wherein the resonantly oscillating, mass-sensitive element (7, 33) is an oscillating crystal or an SAW module.

3. The impactor (1) as claimed in claim 1, wherein the classifying nozzle (2) is removably arranged in the impactor (1) or the impact plate holder (8) is removably arranged in the impactor.

4. The impactor (1) as claimed in claim 1, wherein the impact plate holder (8) bears against or is supported on the classifying nozzle unit (3) or the impact plate holder (8) is radially guided with respect to the axis of a rotating or pivoting movement on the classifying nozzle unit (3).

5. The impactor (1) as claimed in claim 1, wherein the classifying nozzle unit (3) has on a side thereof facing the resonantly oscillating, mass-sensitive element (7, 33) or a guiding element (19) for at least one of radial or axial guidance of the impact plate holder (8).

6. The impactor (1) as claimed in claim 1, wherein the contact pins (23) are electrically connected to the flexible connecting cable (24).

7. The impactor (1) of claim 6, wherein the connecting cable (24) is electrically connected to an evaluation electronics unit for the resonantly oscillating, mass-sensitive element (7, 33).

8. The impactor (1) as claimed in claim 1, wherein the motor (12) is a stepping motor.

9. The impactor (1) as claimed in claim 1, wherein an activation electronics unit or an activation mechanism with which at least one of a change of direction or a limitation of the rotating or pivoting angle of the rotating or pivoting movement is brought about is formed for the rotating or pivoting movement of the impact plate holder (8).

10. The impactor (1) as claimed in claim 1, wherein the impact plate holder (8) has a heating device, and the heating device is connected to the flexible connecting cable (24).

11. The impactor (1) as claimed in claim 1, wherein the classifying nozzle (2) has a through-opening which is arranged eccentrically with respect to the axis, and the classifying nozzle (2) is set up such that it is transversely movable in relation to the line (34) of constant mass sensitivity in order to displace a point of impingement (35, 40) of the carrier gas conducted through the classifying nozzle on the resonantly oscillating, mass-sensitive element (7, 33).

12. The impactor (1) as claimed in claim 1, wherein the classifying nozzle (2) is heatable.

13. The impactor (1) as claimed in claim 1, wherein the impact plate holder (8) is at least radially guided on a motor housing (18) of the motor (12).

14. The impactor (1) as claimed in claim 1, wherein a stop (21) which limits the rotating or pivoting movement of the impact plate holder (8) about the axis with respect to a full circle is formed on a rotatable or pivotable part (8, 9, 10) or on a stationary part (3, 18, 30).

15. The impactor (1) of claim 1, wherein the motor (12) is arranged with the impact plate holder (8) in an outwardly sealed encapsulation (29).

16. A method for characterizing a carrier gas enriched with suspended particles, comprising providing an impactor (1) for analysis of a carrier gas enriched with suspended particles, the impactor including a classifying nozzle unit (3) having at least one classifying nozzle (2) and with just one impact plate (7), the impact plate (7) being formed as a resonantly oscillating, mass-sensitive element (7, 33) and the resonantly oscillating, mass-sensitive element (7, 33) being secured in an impact plate holder (8), the impact plate holder (8) is arranged to be movable in relation to the classifying nozzle (2) by a motor (12), so that a point of impingement (35) of the carrier gas enriched with suspended particles on the impact plate (7) migrates along an arc of a circle or along a circle, a center point coinciding with an axis of a rotating or pivoting movement, on the impact plate (7) and a depositing location of the suspended particles on the resonantly oscillating, mass-sensitive element is changeable during a depositing process, the point of impingement being guided by relative movement along a line of constant mass sensitivity, the resonantly oscillating, mass-sensitive element (7, 33) is electrically connected to a flexible connecting cable (24) that is dimensioned such that the rotating or pivoting movement of the impact plate holder (8) is made possible within a prescribed rotating or pivoting range, and the impact plate holder (8) has a holding plate (17) on which the resonantly oscillating, mass-sensitive element (7, 33) is held, and the impact plate holder (8) has resilient contact pins (23) that are arranged regularly, which in a position for use, act uniformly on the holding plate (17); conducting the carrier gas enriched with suspended particles in the impactor (1) through the classifying nozzle (2) onto the resonantly oscillating, mass-sensitive element (7, 33) such that, as from a prescribed mass, suspended particles are deposited in a depositing process on the resonantly oscillating, mass-sensitive element (7, 33), and determining a mass of the suspended particles deposited on the resonantly oscillating, mass-sensitive element (7, 33) electronically at least one of during the depositing process or between two depositing processes, passing electrical signals at least one of from or to the resonantly oscillating, mass-sensitive element (7, 33) by way of a connecting cable (24), moving the resonantly oscillating, mass-sensitive element (7, 33) in relation to the static classifying nozzle (2) during the depositing process, so that a point of impingement (35) of the carrier gas enriched with suspended particles on the impact plate (7) migrates along the arc of the circle or along the circle, with the center point coinciding with the axis of a rotating or pivoting movement of the impact plate (7), on the impact plate (7) and changing the depositing location of the suspended particles on the resonantly oscillating, mass-sensitive element during the depositing process, the point of impingement being guided by the relative movement along the line of constant mass sensitivity, and at least one of during the depositing process or between two depositing processes, transversely displacing the point of impingement (35) of the carrier gas conducted through the classifying nozzle (2) on the resonantly oscillating, mass-sensitive element (7, 33) in relation to the line of constant mass sensitivity (34).

17. The method as claimed in claim 16, wherein the resonantly oscillating, mass-sensitive element (7, 33) is heated during the depositing process.

18. The method as claimed in claim 16, wherein the resonantly oscillating, mass-sensitive element (7, 33) is rotated or pivoted about an axis in relation to the classifying nozzle, the rotating or pivoting movement being limited with respect to a full circle.

* * * * *